United States Patent
Okada

(10) Patent No.: US 11,555,782 B2
(45) Date of Patent: Jan. 17, 2023

(54) SPECTROMETRY DEVICE AND SPECTROMETRY METHOD

(71) Applicant: YOKOGAWA ELECTRIC CORPORATION, Tokyo (JP)

(72) Inventor: Masanori Okada, Tokyo (JP)

(73) Assignee: YOKOGAWA ELECTRIC CORPORATION, Tokyo (JP)

(*) Notice: Subject to any disclaimer, the term of this patent is extended or adjusted under 35 U.S.C. 154(b) by 864 days.

(21) Appl. No.: 16/460,243

(22) Filed: Jul. 2, 2019

(65) Prior Publication Data

US 2020/0018698 A1 Jan. 16, 2020

(30) Foreign Application Priority Data

Jul. 13, 2018 (JP) ............................. JP2018-133643

(51) Int. Cl.
*G01N 21/39* (2006.01)
*G01N 21/3504* (2014.01)
(Continued)

(52) U.S. Cl.
CPC .............. *G01N 21/39* (2013.01); *G01J 3/027* (2013.01); *G01J 3/28* (2013.01); *G01J 3/42* (2013.01); *G01J 3/433* (2013.01); *G01N 21/31* (2013.01); *G01N 21/3504* (2013.01); *G01N 21/64* (2013.01); *G01N 21/6402* (2013.01);
(Continued)

(58) Field of Classification Search
CPC .... G01N 21/39; G01N 21/31; G01N 21/3504; G01N 21/64; G01N 21/6402; G01N 21/65; G01N 33/0004; G01N 2021/1753; G01N 2021/3125; G01N 2021/3159; G01N 2021/3196; G01N 2021/399; G01N 2021/6417; G01N 2021/655; G01N 2021/612; G01J 3/027; G01J 3/28;
(Continued)

(56) References Cited

U.S. PATENT DOCUMENTS 3,958,122 A * 5/1976 Jowett ................ G01N 21/3504
250/344
4,849,637 A * 7/1989 Cerff ...................... G01N 21/39
250/343
(Continued)

FOREIGN PATENT DOCUMENTS

CN 101131348 A 2/2008
CN 102735644 A 10/2012
(Continued)

OTHER PUBLICATIONS

Machine translation of JPS62157537A (Year: 1985).*
Extended European Search Report issued in corresponding European Application No. 19186139.2 dated Dec. 13, 2019 (8 pages).

*Primary Examiner* — Dominic J Bologna
(74) *Attorney, Agent, or Firm* — Osha Bergman Watanabe & Burton LLP

(57) ABSTRACT

A spectrometry device includes a switch and a converter. The switch acquires a first reception signal and a second reception signal that respectively include information relating to an optical spectrum and switches between outputting the first reception signal and outputting the second reception signal based on control by a controller. The converter converts the first reception signal or the second reception signal output from the switch into a digital signal.

11 Claims, 7 Drawing Sheets

(51) Int. Cl.
  *G01N 33/00* (2006.01)
  *G01J 3/02* (2006.01)
  *G01J 3/28* (2006.01)
  *G01J 3/433* (2006.01)
  *G01J 3/42* (2006.01)
  *G01N 21/31* (2006.01)
  *G01N 21/64* (2006.01)
  *G01N 21/65* (2006.01)
  *G01N 21/17* (2006.01)

(52) U.S. Cl.
  CPC ......... *G01N 21/65* (2013.01); *G01N 33/0004* (2013.01); *G01J 2003/423* (2013.01); *G01J 2003/4334* (2013.01); *G01N 2021/1753* (2013.01); *G01N 2021/3125* (2013.01); *G01N 2021/3159* (2013.01); *G01N 2021/3196* (2013.01); *G01N 2021/399* (2013.01); *G01N 2021/6417* (2013.01); *G01N 2021/655* (2013.01); *G01N 2201/0612* (2013.01)

(58) Field of Classification Search
  CPC ........ G01J 3/42; G01J 3/433; G01J 2003/423; G01J 2003/4334
  See application file for complete search history.

(56) References Cited

U.S. PATENT DOCUMENTS

| | | |
|---|---|---|
| 4,914,719 A | 4/1990 | Conlon et al. |
| 10,768,046 B2* | 9/2020 | Okada ................ G01N 21/3504 |
| 2011/0019193 A1* | 1/2011 | Danno .................. G01J 3/4338 |
| | | 356/433 |
| 2011/0276294 A1* | 11/2011 | Ota ...................... G01R 35/005 |
| | | 702/85 |

FOREIGN PATENT DOCUMENTS

| | | |
|---|---|---|
| DE | 4023649 A1 | 2/1991 |
| JP | S51-88290 A | 8/1976 |
| JP | S62-157537 A | 7/1987 |
| JP | S63-165735 A | 7/1988 |
| JP | H02-17429 A | 1/1990 |
| JP | 2015-137910 A | 7/2015 |

* cited by examiner

SPECTROMETRY DEVICE AND SPECTROMETRY METHOD

CROSS-REFERENCE TO RELATED APPLICATIONS

This application is based on and claims priority under 35 U.S.C. § 119 from Japanese Patent Application No. 2018-133643 filed on Jul. 13, 2018, the contents of which are incorporated herein by reference.

BACKGROUND

Technical Field

The present invention generally relates to a spectrometry device and a spectrometry method.

Related Art

Conventional technologies of spectroscopically acquiring information relating to an analysis target based on an optical spectrum such as an absorption spectrum are known.

For example, patent literature 1 discloses an insertable gas-concentration measuring device that can simultaneously analyze with one device two types of gas components of different analytical wavelengths using two light sources and two photodetectors respectively corresponding to the two light sources.

Patent Literature 1: Japanese Patent Application Publication No. 2015-137910

Such a spectrometry device may further have reference cells for detecting wavelength positions of the absorption-spectrum peaks of the analysis-target components and photodetectors for reference lights transmitted through the reference cells. That is, for each of the two types of gas components, a pair of photodetectors is disposed—one for the measurement light and one for the reference light—such that the spectrometry device has a total of four photodetectors.

At this time, when each photodetector is connected with a conversion unit that converts a reception signal output from the photodetector from an analog signal into a digital signal, product costs increase and a circuit system for processing the reception signals becomes complex.

SUMMARY

One or more embodiments provide a spectrometry device and a spectrometry method that can reduce product costs even in a situation of processing two reception signals for each analysis-target component.

A spectrometry device according to one or more embodiments includes a switching unit that acquires a first reception signal and a second reception signal that respectively include information relating to an optical spectrum and switches between outputting the first reception signal and outputting the second reception signal based on control by a control unit and a conversion unit that converts the first reception signal or the second reception signal output from the switching unit into a digital signal. According to such a spectrometry device, two reception signals can be processed by one conversion unit. As such, product costs can be reduced. More specifically, in the spectrometry device, by the switching unit adjusting an output timing of each reception signal according to time division, two reception signals are digitized by one conversion unit. Therefore, a number of conversion-unit-related circuit components is reduced compared to the prior art, which requires two conversion units.

In a spectrometry device according to one or more embodiments, the control unit may control the switching unit so a second time period that is a time period when the second reception signal is repeatedly output to the conversion unit is shorter than a first time period that is a time period when the first reception signal is repeatedly output to the conversion unit. In this manner, by the control unit weighting switching times of the switching unit according to two reception signals, an analysis period based on the first reception signal is shortened. Even in a situation of respectively processing the first reception signal and the second reception signal, the analysis period based on the first reception signal, which is crucial for the spectrometry device, is shortened. This improves an analysis efficiency by the spectrometry device.

In a spectrometry device according to one or more embodiments, the control unit may analyze an optical spectrum based on the first reception signal converted by the conversion unit during the first time period when a time elapsed from output from the switching unit switching to the first reception signal reaches the first time period. This enables analysis of the optical spectrum based on the first reception signal using the information relating to the optical spectrum repeatedly included during the first time period. Therefore, by executing signal processing such as averaging, a precision of analysis using the optical spectrum improves.

In a spectrometry device according to one or more embodiments, the control unit may determine whether added repetition of the second time period arrives at a predetermined time period set in advance and analyzes an optical spectrum based on the converted second reception signal during the added repetition of the second time period when it is determined that the added repetition of the second time period arrived at the predetermined time. As with the above first reception signal, this enables analysis of the optical spectrum based on the second reception signal using the information relating to the optical spectrum repeatedly included during the added repetition of the second time. Therefore, by executing signal processing such as averaging, a precision of analysis using the optical spectrum likewise improves.

In a spectrometry device according to one or more embodiments, the predetermined time period may be equal to the first time period. This enables the spectrometry device to analyze the optical spectrum based on the second reception signal at an SN ratio equal to an optical-spectrum SN ratio based on the first reception signal in a situation where SN ratios due to an optical system are equal between the first reception signal and the second reception signal. Therefore, a precision of analysis using the optical spectrum improves.

In a spectrometry device according to one or more embodiments, the first reception signal may include information relating to an absorption spectrum of an analysis-target component in a gas to be measured and the second reception signal may include information on an absorption spectrum of a gas that is identical to the analysis-target component in the gas to be measured and has a known concentration. For example, in another spectrometry method such as fluorescence spectrometry or Raman spectrometry, an intensity of a measurement light of a fluorescent light or a Raman light is weak and the measurement light is not easily detected. In contrast, by using an absorption spectrometry method, the intensity of the measurement light is increased and the measurement light is easily detected. Therefore, the spectrometry device can easily calculate an optical spectrum.

A spectrometry method according to one or more embodiments is a spectrometry method by a spectrometry device, including a step of acquiring a first reception signal and a second reception signal that respectively include information relating to an optical spectrum and switching between outputting the first reception signal and outputting the second reception signal and a step of converting the switched-to first reception signal or second reception signal into a digital signal. According to such a spectrometry method, two reception signals can be processed by switching output. As such, products costs can be reduced. More specifically, in the spectrometry method, by adjusting an output timing of each reception signal according to time division, two reception signals can be digitized using one conversion unit. Therefore, a number of conversion-unit-related circuit components is reduced compared to the prior art, which requires two conversion units.

In a spectrometry method according to one or more embodiments, at the step of converting into the digital signal, a second time period that is a time period when the second reception signal is repeated may be shorter than a first time period that is a time period when the first reception signal is repeated. In this manner, by weighting switching times according to two reception signals, an analysis period based on the first reception signal is shortened. Even in a situation of respectively processing the first reception signal and the second reception signal, the analysis period based on the first reception signal, which is crucial for the spectrometry device, is shortened. This improves an analysis efficiency by the spectrometry device.

In a spectrometry method according to one or more embodiments, further included may be a step of analyzing an optical spectrum based on the first reception signal converted into the digital signal during the first time period when a time elapsed from switching to the first reception signal reaches the first time period. This enables analysis of the optical spectrum based on the first reception signal using the information relating to the optical spectrum repeatedly included during the first time period. Therefore, by executing signal processing such as averaging, a precision of analysis using the optical spectrum improves.

In a spectrometry method according to one or more embodiments, further included may be a step of determining whether an added repetition of the second time period arrives at a predetermined time period set in advance and a step of analyzing an optical spectrum based on the converted second reception signal during the added repetition of the second time period when it is determined that the added repetition of the second time period arrived at the predetermined time. As with the above first reception signal, this enables analysis of the optical spectrum based on the second reception signal using the information relating to the optical spectrum repeatedly included during the added repetition of the second time period. Therefore, by executing signal processing such as averaging, a precision of analysis using the optical spectrum likewise improves.

In a spectrometry method according to one or more embodiments, the predetermined time period may be equal to the first time period. This enables analysis of the optical spectrum based on the second reception signal at an SN ratio equal to an optical-spectrum SN ratio based on the first reception signal in a situation where SN ratios due to an optical system are equal between the first reception signal and the second reception signal. Therefore, a precision of analysis using the optical spectrum improves.

In a spectrometry method according to one or more embodiments, the first reception signal may include information relating to an absorption spectrum of an analysis-target component in a gas to be measured and the second reception signal may include information on an absorption spectrum of a gas that is identical to the analysis-target component in the gas to be measured and has a known concentration. For example, in another spectrometry method such as fluorescence spectrometry or Raman spectrometry, an intensity of a measurement light of a fluorescent light or a Raman light is weak and the measurement light is not easily detected. In contrast, by using an absorption spectrometry method, the intensity of the measurement light is increased and the measurement light is easily detected. Therefore, in the spectrometry method according to one or more embodiments, the optical spectrum can be easily calculated.

In one or more embodiments, a spectrometry device includes a switch and a converter. The switch acquires a first reception signal and a second reception signal that respectively include information relating to an optical spectrum and switches between outputting the first reception signal and outputting the second reception signal based on control by a controller. The converter converts the first reception signal or the second reception signal output from the switch into a digital signal.

In one or more embodiments, a spectrometry method by a spectrometry device includes acquiring a first reception signal and a second reception signal that respectively include information relating to an optical spectrum, switching between outputting the first reception signal and outputting the second reception signal, and converting the switched-to first reception signal or second reception signal into a digital signal.

According to one or more embodiments, a spectrometry device and a spectrometry method that can reduce product costs even in a situation of processing two reception signals for each analysis-target component can be provided.

DETAILED DESCRIPTION

Figure 1:
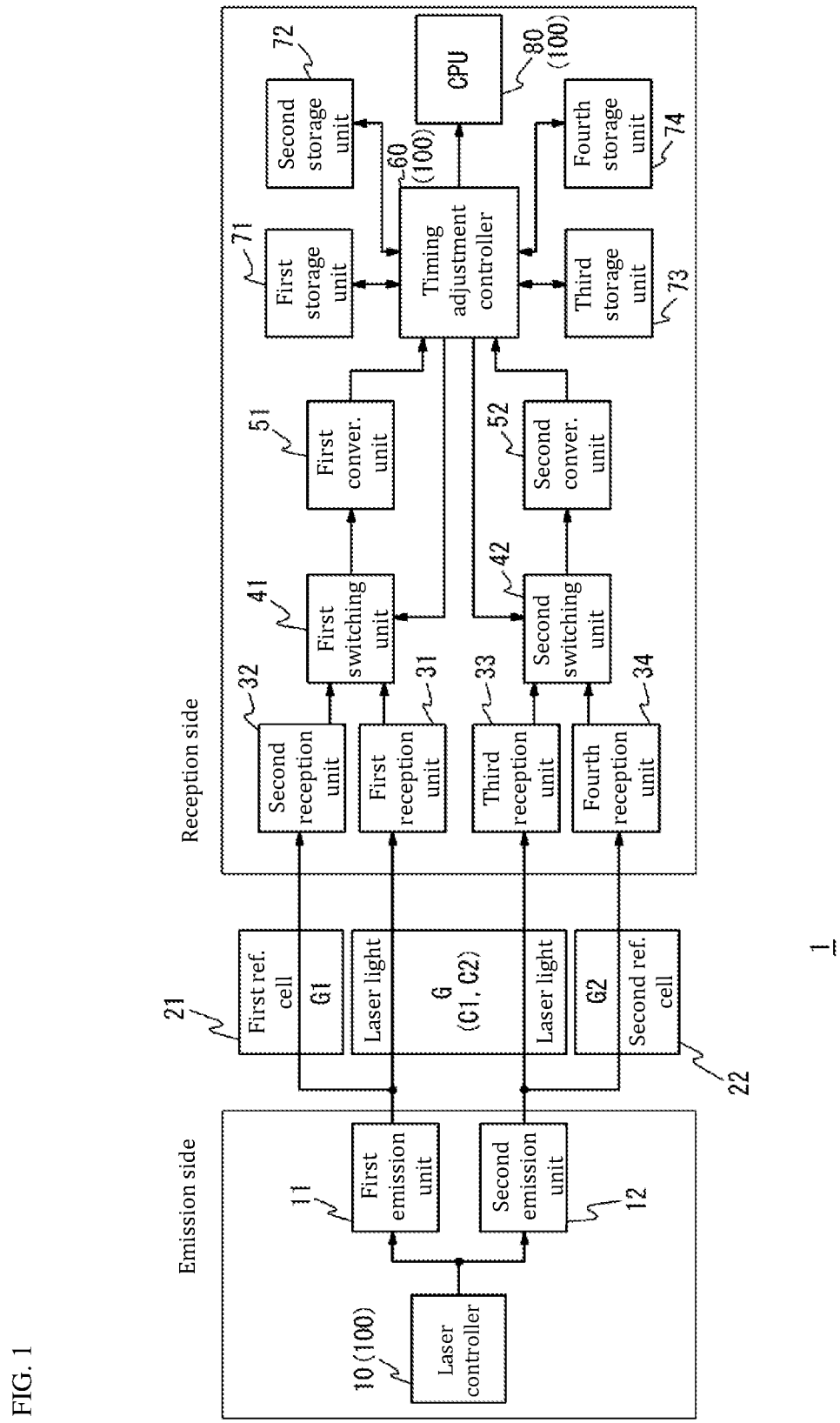
FIG. 1 is a block diagram illustrating one example of a spectrometry device according to one or more embodiments.

Embodiments of the present invention will be described after a brief discussion of conventional art.

A laser gas analyzer is directly installed to a flow path wherein a gas to be measured such as a process gas flows, and concentration analysis of an analysis-target component is performed. The gas to be measured includes gas molecules of, for example, CO (carbon monoxide), $CO_2$ (carbon dioxide), $H_2O$ (water), $C_nH_m$ (a hydrocarbon), $NH_3$ (ammonia), and $O_2$ (oxygen). The flow path includes piping, a flue, a combustion furnace, and the like.

Such a laser gas analyzer includes, for example, a TDLAS (tunable diode laser absorption spectroscopy) laser gas analyzer. A TDLAS laser gas analyzer analyzes the concentration of the analysis-target component by, for example, irradiating a laser light into the gas to be measured.

The gas molecules included in the gas to be measured exhibit an absorption spectrum based on molecular vibration and molecular rotational-energy transitioning in an infrared to near-infrared region. The absorption spectrum is specific to the component molecules. According to the Beer-Lambert law, an absorbance of the laser light by the gas molecules is proportional to the component concentration thereof and an optical-path length. Therefore, the concentration of the analysis-target component can be analyzed by measuring an intensity of the absorption spectrum.

In TDLAS, a semiconductor laser light of a linewidth sufficiently narrower than an energy-transition absorption linewidth had by the gas molecules is irradiated to the gas to be measured. By subjecting an injection current of the semiconductor laser to high-speed modulation, an emission wavelength thereof is swept. By measuring an intensity of the semiconductor laser light transmitted through the gas to be measured, one independent absorption spectrum is measured.

A sweeping range of the semiconductor laser light differs according to use. In a situation where the analysis-target component is $O_2$, the linewidth of the semiconductor laser light is, for example, 0.0002 nm and a sweeping width is, for example, 0.1 to 0.2 nm. The absorption spectrum is measured by sweeping the sweeping width of 0.1 to 0.2 nm. The concentration of the analysis-target component is sought by performing a concentration conversion from the acquired one absorption spectrum. A method of the concentration conversion includes known methods such as a peak-height method, a spectrum-area method, and a 2f method.

Generally, an emission wavelength of a semiconductor laser depends on an injection current and a temperature of the semiconductor laser. For example, the emission wavelength becomes longer the greater the injection current. For example, the emission wavelength becomes longer the higher the temperature.

In performing measurement by TDLAS, a temperature of the semiconductor laser is adjusted so the emission wavelength of the semiconductor laser roughly matches a wavelength band of the absorption spectrum that is wanting to be measured. The temperature of the semiconductor laser is maintained at the adjusted value. Afterward, the injection current of the semiconductor laser is changed to perform fine adjustment of the emission wavelength.

Here, a conventional method of measuring the absorption spectrum of the gas to be measured by repeatedly sweeping the emission wavelength of the semiconductor laser is described with reference to FIGS. 6A to 6C.

Figure 6A:
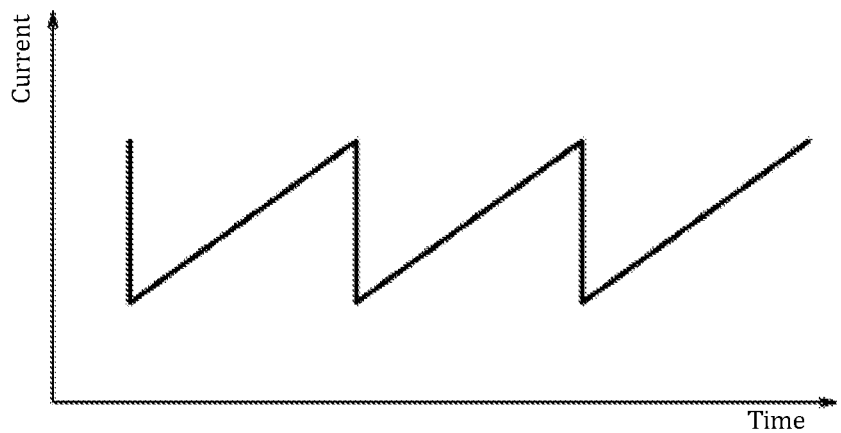
FIG. 6A is a schematic diagram illustrating an injection current of a repeatedly swept semiconductor laser.

FIG. 6A is a schematic diagram illustrating the injection current of the repeatedly swept semiconductor laser. When the emission wavelength of the semiconductor laser matches the wavelength band of the absorption spectrum wanting to be measured, the emission wavelength of the semiconductor laser is repeatedly swept in this wavelength band. At this time, the injection current of the semiconductor laser is repeatedly swept. For example, the injection current of the semiconductor laser exhibits a sawtooth waveform.

Figure 6B:
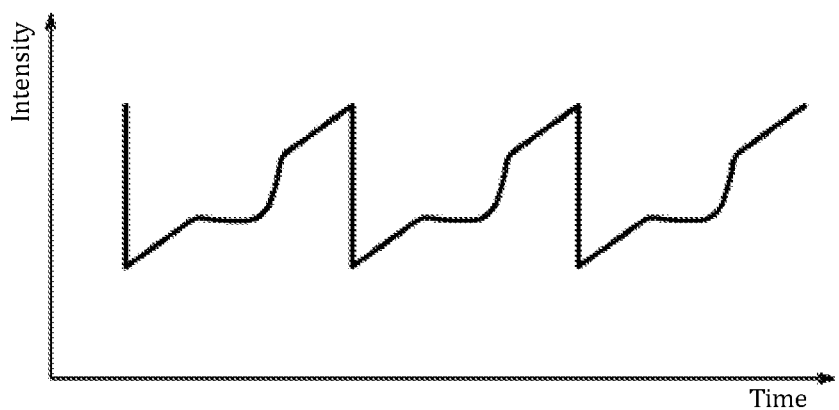
FIG. 6B is a schematic diagram illustrating a change in an intensity of a semiconductor laser light transmitted through a gas to be measured.
Figure 6C:
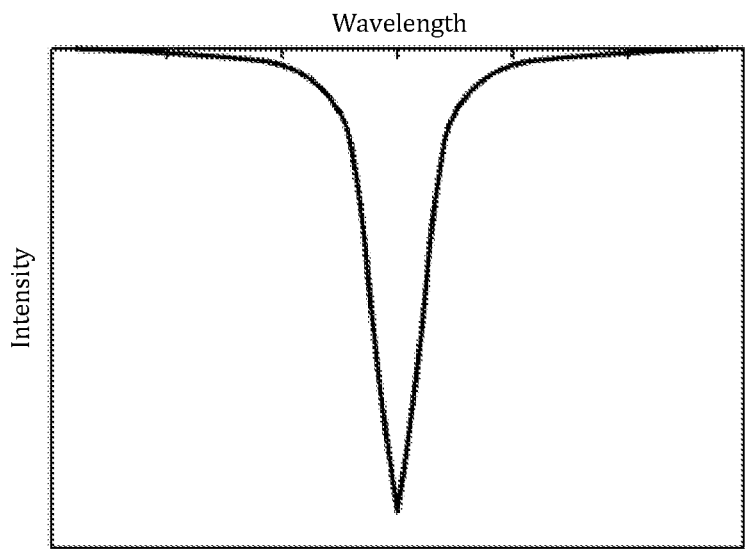
FIG. 6C is a schematic diagram illustrating a calculated absorption spectrum of the gas to be measured.

FIG. 6B is a schematic diagram illustrating a change in the intensity of the semiconductor laser light transmitted through the gas to be measured. The semiconductor laser light whose emission wavelength is repeatedly swept is transmitted through the gas to be measured and condensed to a reception unit. The reception unit outputs a reception signal such as that illustrated in FIG. 6B that reflects a light absorption amount of the gas to be measured at each wavelength of the semiconductor laser light. At this time, the irradiation intensity of the semiconductor laser light also changes in conjunction with the sweeping of the injection current of the semiconductor laser. For example, the irradiation intensity becomes higher the greater the injection current. Therefore, based on the change in the irradiation intensity accompanying the sweeping of the injection current and the change in the light absorption amount of the gas to be measured at each wavelength, the reception signal output from the light receiving unit exhibits a waveform where a dip is superimposed on a sawtooth waveform.

Then, based on the reception signal illustrated in FIG. 6B, the absorption spectrum of the gas to be measured is calculated. FIG. 6C is a schematic diagram illustrating the calculated absorption spectrum of the gas to be measured. The absorption spectrum is calculated by, for example, subtracting a reception signal of a situation where the semiconductor laser light is not transmitted through the gas to be measured from the reception signal of the situation where the semiconductor laser light is transmitted through the gas to be measured and making the vertical axis a logarithm. An absorbance exhibited by such an absorption spectrum is proportional to the component concentration of the gas to be measured. For example, an area of the absorption spectrum is proportional to the component concentration of the gas to be measured. Therefore, the component concentration of the gas to be measured can be calculated based on the absorbance.

Figure 7:
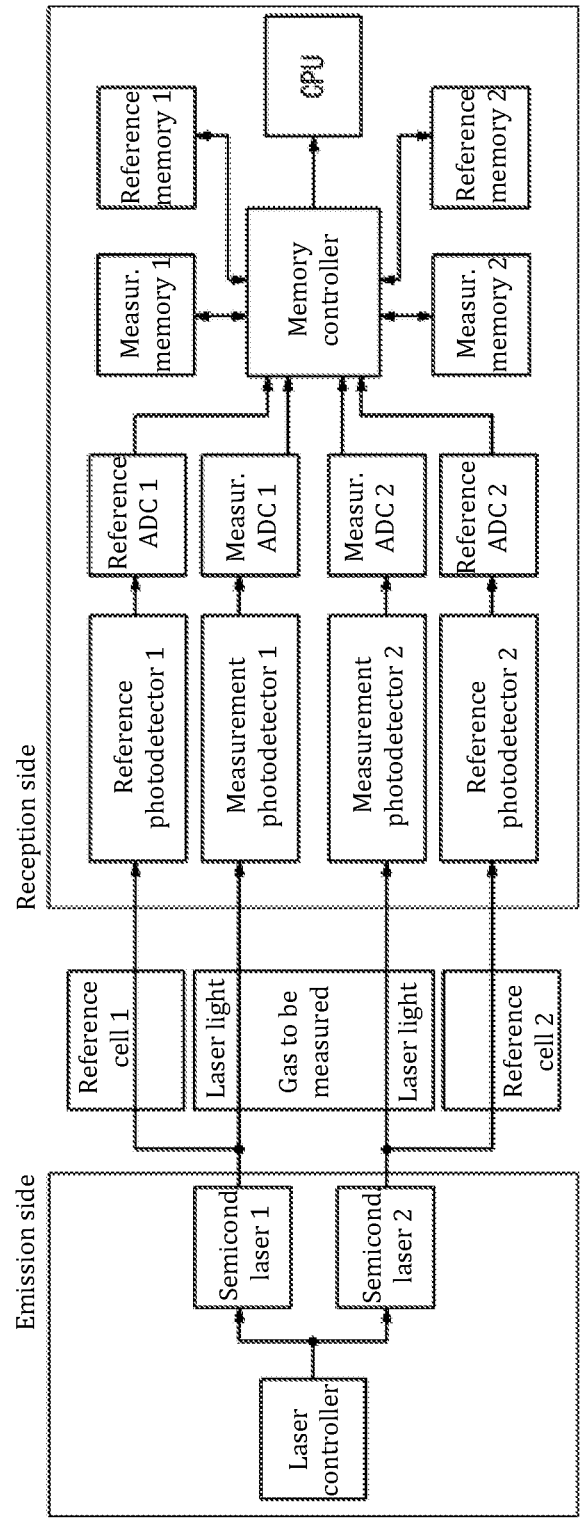
FIG. 7 is a block diagram illustrating a conventional spectrometry device used in spectrometry of two types of analysis-target components of different analytical wavelengths.

FIG. 7 is a block diagram illustrating a conventional spectrometry device used in spectrometry of two types of analysis-target components of different analytical wavelengths.

Conventionally, two semiconductor lasers are used to perform spectrometry on two types of analysis-target components of different analytical wavelengths. An irradiation light irradiated from one semiconductor laser is split into two. One split irradiation light is transmitted through the gas to be measured and detected by a measurement photodetector as a measurement light. The other split irradiation light is transmitted through a reference cell and detected by a reference photodetector as a reference light.

A circuit system configuring a reception side has the measurement photodetector, a measurement ADC (analog/digital converter), and a measurement memory and the reference photodetector, a reference ADC, and a reference memory for each semiconductor laser. In this manner, each photodetector is connected with an ADC that converts a reception signal output from the photodetector from an analog signal into a digital signal. With the conventional spectrometry device, which requires four ADCs for four photodetectors, product costs increase and the circuit system for processing the reception signals becomes complex.

One or more embodiments provide a spectrometry device 1 that can reduce product costs even in a situation of processing two reception signals—one based on a measurement light and one based on a reference light—for each analysis-target component. One or more embodiments will be mainly described below while referring to the included drawings.

FIG. 1 is a block diagram illustrating one example of a configuration of the spectrometry device 1 according to one or more embodiments. The spectrometry device 1 can irradiate two types of irradiation lights of different wavelength bands in parallel to a gas G to be measured and, based on reception signals processed in different reception circuits, analyze in parallel different analysis-target components in the gas G to be measured.

As illustrated in FIG. 1, the spectrometry device 1 has a laser controller 10, a first emission unit 11, and a second emission unit 12 that configure an emission side.

The laser controller 10 configures a portion of a control unit 100 of the spectrometry device 1 that is described below. The laser controller 10 is connected to the first emission unit 11 and the second emission unit 12 and controls operations thereof. For example, the laser controller 10 generates an emission-wavelength control signal and controls emission wavelengths of irradiation lights respectively irradiated from the first emission unit 11 and the second emission unit 12. The laser controller 10 additionally controls, for example, turning respective irradiation by the first emission unit 11 and the second emission unit 12 on and off, irradiation intensities, and the like.

The first emission unit 11 and the second emission unit 12 each have, for example, any light source that can measure the gas G to be measured by TDLAS. The gas G to be measured includes gas molecules of, for example, CO, $CO_2$, $H_2O$, $C_nH_m$, $NH_3$, and $O_2$. Each emission unit has, for example, a semiconductor laser. Based on an injection current output from the laser controller 10, each emission unit irradiates a light whose emission wavelength is swept to the gas G to be measured. At this time, each emission unit may irradiate a light whose emission wavelength is swept in the same wavelength range over a plurality of periods. The emission wavelength of the first emission unit 11 and the emission wavelength of the second emission unit 12 respectively correspond to analytical wavelengths of two types of different analysis-target components C1 and C2 included in the gas G to be measured and are different from each other.

The spectrometry device 1 further has a first reference cell 21. The irradiation light irradiated from the first emission unit 11 is split into two. One split irradiation light is transmitted through the gas G to be measured. The other split irradiation light is transmitted through a gas G1 that is enclosed in the first reference cell 21, is identical to the analysis-target component C1 in the gas G to be measured, and has a known concentration.

The spectrometry device 1 further has a second reference cell 22. The irradiation light irradiated from the second emission unit 12 is split into two. One split irradiation light is transmitted through the gas G to be measured. The other split irradiation light is transmitted through a gas G2 that is enclosed in the second reference cell 22, is identical to the analysis-target component C2 in the gas G to be measured, and has a known concentration.

The spectrometry device 1 has components configuring a reception side. More specifically, the spectrometry device 1 has a first reception unit 31, a second reception unit 32, a third reception unit 33, and a fourth reception unit 34; a first switching unit 41 and a second switching unit 42; and a first conversion unit 51 and a second conversion unit 52. The spectrometry device 1 further has a timing adjustment controller 60; a first storage unit 71, a second storage unit 72, a third storage unit 73, and a fourth storage unit 74; and a CPU (central processing unit) 80. Together with the above laser controller 10, the timing adjustment controller 60 and the CPU 80 configure the control unit 100 of the spectrometry device 1.

The first reception unit 31 and the third reception unit 33 each have, for example, any photodetector that can measure the gas G to be measured by TDLAS. Each reception unit has, for example, a photodiode. Each reception unit detects and converts into an electrical measurement signal a measurement light including information relating to an optical spectrum of the gas G to be measured. The optical spectrum includes, for example, an absorption spectrum.

The second reception unit 32 and the fourth reception unit 34 have, for example, any photodetector that can respectively measure the gas G1 and the gas G2 enclosed in the first reference cell 21 and the second reference cell 22 by TDLAS. Each reception unit has, for example, a photodiode. Each reception unit detects and converts into an electrical reference signal a reference light including information relating to an optical spectrum of each gas enclosed in the reference cells. The optical spectrum includes, for example, an absorption spectrum.

The first reception unit 31 detects the portion of the irradiated light that is irradiated from the first emission unit 11 and transmitted through the gas G to be measured as the measurement light. When the first reception unit 31 detects the measurement light, the first reception unit 31 outputs a first reception signal S1 including information relating to an optical spectrum of the analysis-target component C1. The second reception unit 32 detects the portion of the irradiated light that is irradiated from the first emission unit 11 and transmitted through the first reference cell 21 as the reference light. When the second reception unit 32 detects the reference light, the second reception unit 32 outputs a second reception signal S2 including information relating to the optical spectrum of the gas G1.

Likewise, the third reception unit 33 detects the portion of the irradiated light that is irradiated from the second emission unit 12 and transmitted through the gas G to be measured as the measurement light. When the third reception unit 33 detects the measurement light, the third reception unit 33 outputs a third reception signal S3 including information relating to an optical spectrum of the analysis-target component C2. The fourth reception unit 34 detects the portion of the irradiated light that is irradiated from the second emission unit 12 and transmitted through the second reference cell 22 as the reference light. When the fourth reception unit 34 detects the reference light, the fourth reception unit 34 outputs a fourth reception signal S4 including information relating to the optical spectrum of the gas G2.

The first switching unit 41 has any signal switching circuit such as a switch. The first switching unit 41 is connected to the first reception unit 31 and the second reception unit 32. The first switching unit 41 acquires the first reception signal S1 and the second reception signal S2 respectively output from the first reception unit 31 and the second reception unit 32. Based on control by the timing adjustment controller 60 of the control unit 100, the first switching unit 41 switches between output of the first reception signal 51 and output of the second reception signal S2.

Likewise, the second switching unit 42 has any signal switching circuit such as a switch. The second switching unit 42 is connected to the third reception unit 33 and the fourth reception unit 34. The second switching unit 42 acquires the third reception signal S3 and the fourth reception signal S4 respectively output from the third reception unit 33 and the fourth reception unit 34. Based on control by the timing adjustment controller 60 of the control unit 100, the second switching unit 42 switches between output of the third reception signal S3 and output of the fourth reception signal S4.

The first conversion unit 51 has, for example, an ADC. The first conversion unit 51 is connected to the first switching unit 41. The first conversion unit 51 converts the first reception signal S1 or the second reception signal S2 output from the first switching unit 41 from an analog signal into a digital signal.

Likewise, the second conversion unit 52 has, for example, an ADC. The second conversion unit 52 is connected to the second switching unit 42. The second conversion unit 52 converts the third reception signal S3 or the fourth reception signal S4 output from the second switching unit 42 from an analog signal into a digital signal.

The timing adjustment controller 60 is connected to the first conversion unit 51 and the second conversion unit 52. The timing adjustment controller 60 acquires the first reception signal S1 or the second reception signal S2 output from the first conversion unit 51. Likewise, the timing adjustment controller 60 acquires the third reception signal S3 or the fourth reception signal S4 output from the second conversion unit 52.

The timing adjustment controller 60 is also connected to the first switching unit 41. The timing adjustment controller 60 controls an output time, a timing, and the like of the first reception signal S1 or the second reception signal S2 output from the first switching unit 41 to the first conversion unit 51 and outputs the first reception signal S1 or the second reception signal S2 to the first conversion unit 51 in a time-divided state.

Likewise, the timing adjustment controller 60 is also connected to the second switching unit 42. The timing adjustment controller 60 controls an output time, a timing, and the like of the third reception signal S3 or the fourth reception signal S4 output from the second switching unit 42 to the second conversion unit 52 and outputs the third reception signal S3 or the fourth reception signal S4 to the second conversion unit 52 in a time-divided state.

The first storage unit 71, the second storage unit 72, the third storage unit 73, and the fourth storage unit 74 are connected to the timing adjustment controller 60. Each storage unit has any storage device such as an HDD (hard disk drive), an SSD (solid-state drive), an EEPROM (electrically erasable programmable read-only memory), a ROM (read-only memory), or a RAM (random access memory). Each storage unit may function as, for example, a main storage device, an auxiliary storage device, or a cache memory. Each storage unit is not limited to being built into the spectrometry device 1 and may be an external storage device connected by, for example, a digital input/output port such as a USB port.

The first storage unit 71 stores, as necessary, data based on the first reception signal S1 digitized by the first conversion unit 51. The second storage unit 72 stores, as necessary, data based on the second reception signal S2 digitized by the first conversion unit 51. The third storage unit 73 stores, as necessary, data based on the third reception signal S3 digitized by the second conversion unit 52. The fourth storage unit 74 stores, as necessary, data based on the fourth reception signal S4 digitized by the second conversion unit 52.

The CPU 80 is connected to the first storage unit 71, the second storage unit 72, the third storage unit 73, and the fourth storage unit 74 via the timing adjustment controller 60. The CPU 80 determines, for example, whether a data acquisition time based on each reception signal by the timing adjustment controller 60 is arrived at a predetermined time that includes a defined sweeping count. When the CPU 80 determines that the data acquisition time is arrived at the predetermined time, the CPU 80 acquires the data from the corresponding storage unit and analyzes the optical spectrum based on the corresponding reception signal.

The CPU 80 subjects the acquired reception signal to any signal processing. For example, the CPU 80 may average the acquired reception signal over a plurality of periods. Averaging signifies adding signal strengths of the same wavelength portion of the sweeping waveform for each period and dividing by a total sweeping count. The CPU 80 may calculate the absorption spectrum from the acquired reception signal in this manner.

The control unit 100 that includes the laser controller 10, the timing adjustment controller 60, and the CPU 80 includes one or more processors. More specifically, the control unit 100 includes any processor such as a dedicated processor that can realize various types of control, processing, and the like by the above laser controller 10, timing adjustment controller 60, and CPU 80.

The control unit 100 is connected to each component that is controlled by the spectrometry device 1, controlling and managing these components. For example, the laser controller 10 is connected to the first emission unit 11 and the second emission unit 12, controlling and managing such. For example, the timing adjustment controller 60 is connected to the first switching unit 41 and the second switching unit 42 and the first storage unit 71, the second storage unit 72, the third storage unit 73, and the fourth storage unit 74, controlling and managing such.

The control unit 100 executes the signal processing as necessary based on the acquired data and analyzes the optical spectrum. For example, the CPU 80 is connected to each storage unit via the timing adjustment controller 60, acquires the data from the corresponding storage unit, processes the corresponding reception signal, and analyzes the calculated absorption spectrum.

Figure 2:
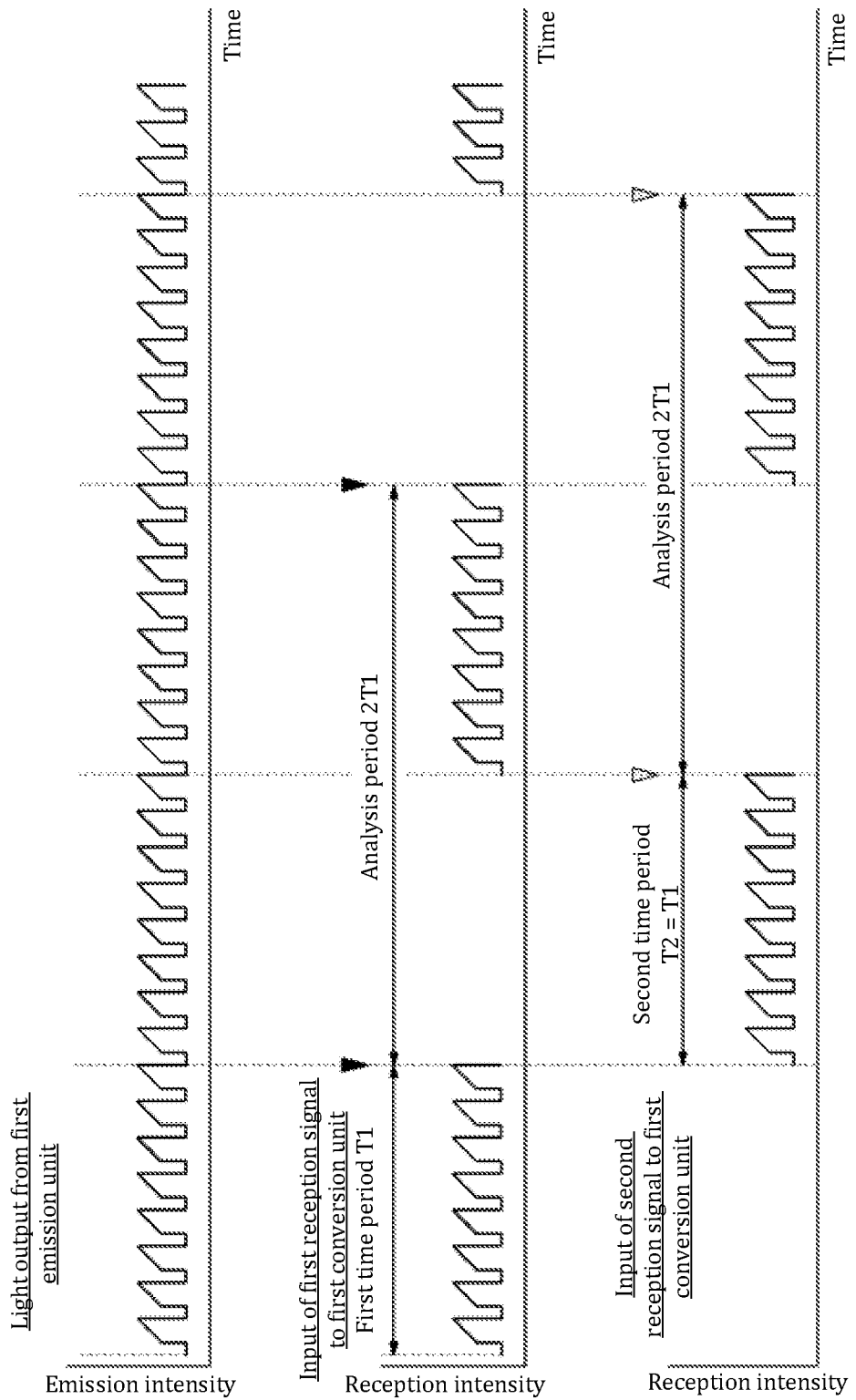
FIG. 2 is a schematic diagram illustrating a first example of control and processing executed by a control unit.
Figure 3:
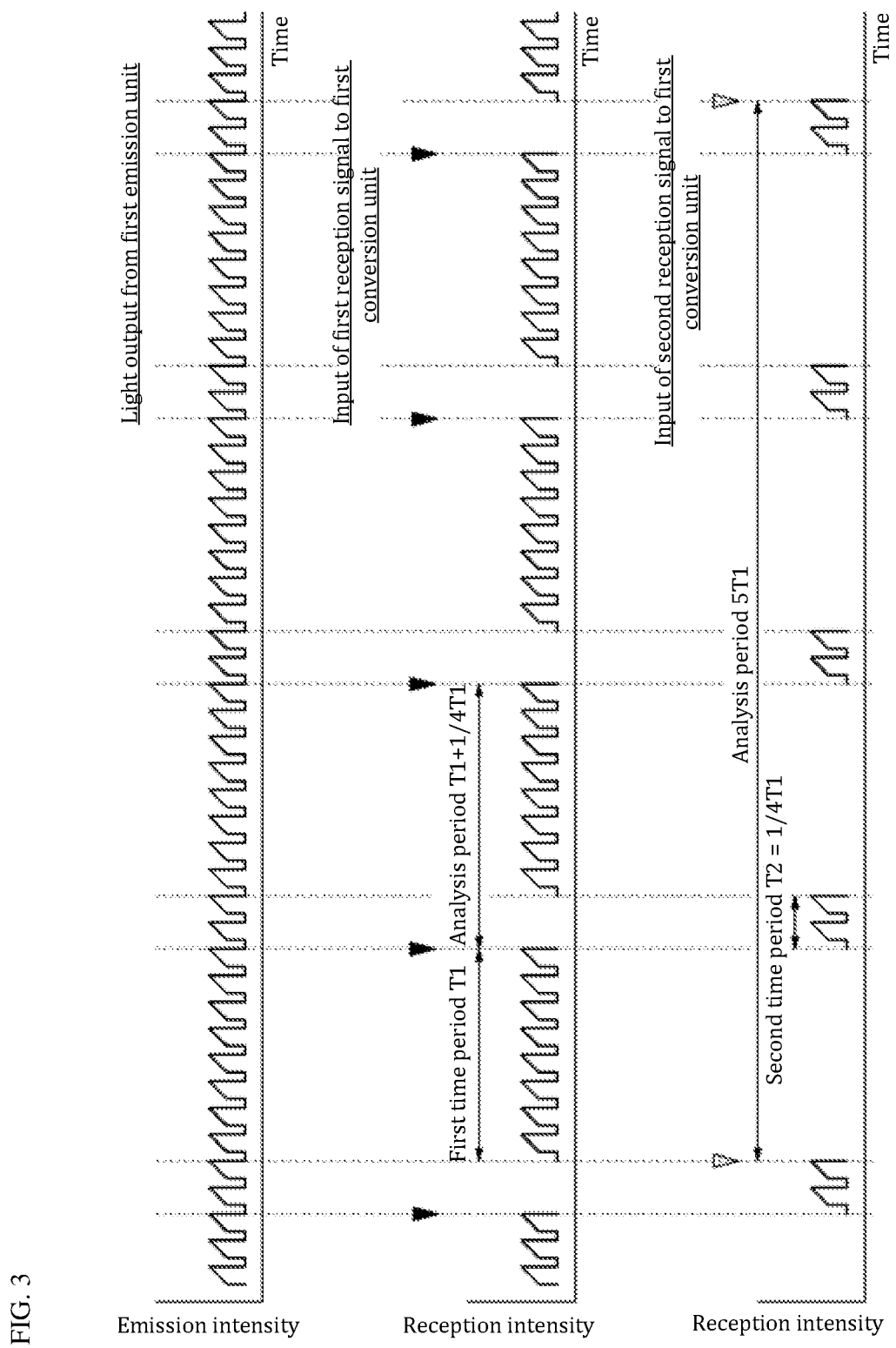
FIG. 3 is a schematic diagram illustrating a second example of the control and processing executed by the control unit.
Figure 4:
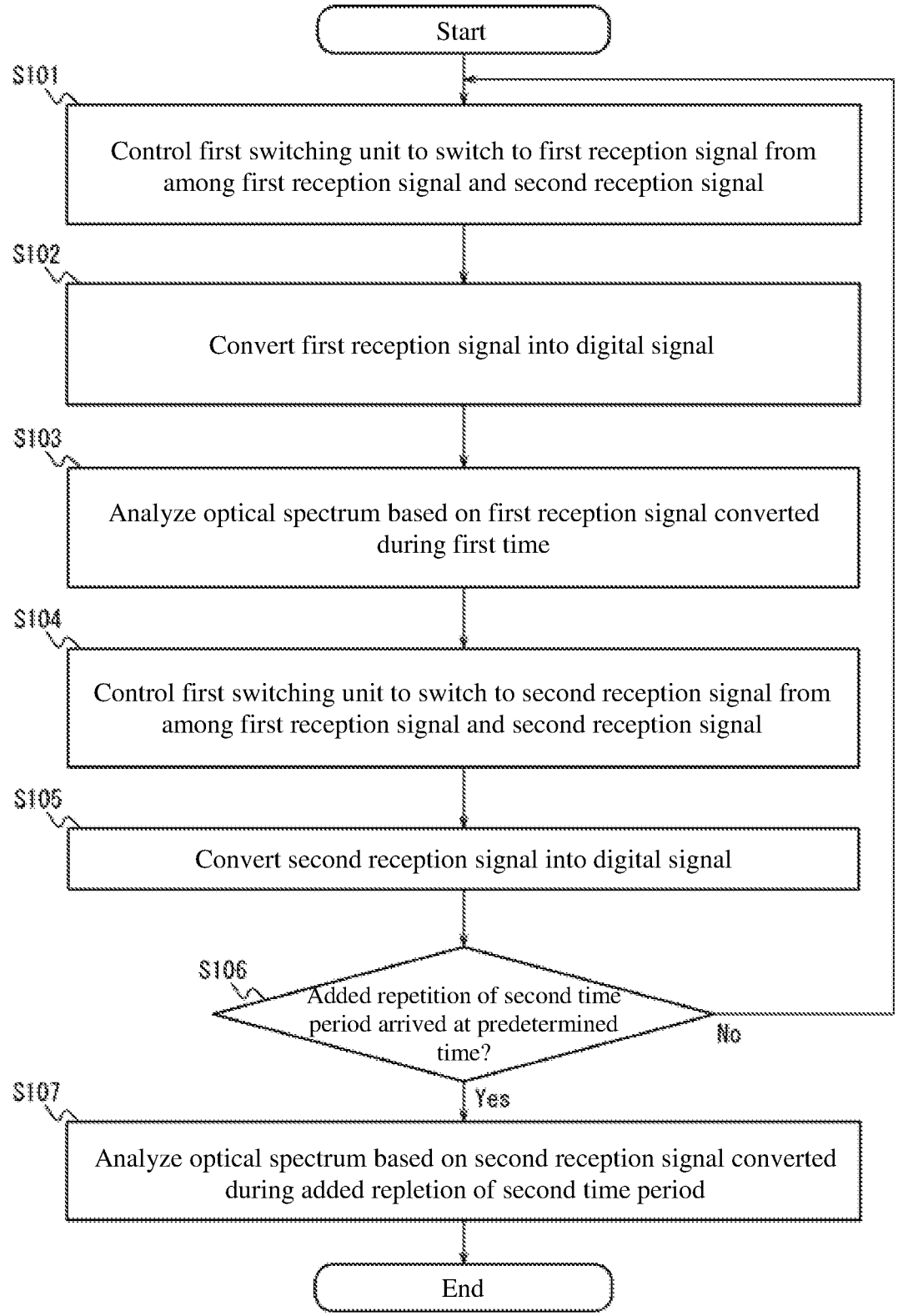
FIG. 4 is a flowchart illustrating one example of processing performed by the spectrometry device of FIG. 1.

Next, the controls and processes executed by the control unit 100—for example, the timing adjustment controller 60 and the CPU 80—are mainly described while referring to FIGS. 2 to 4.

FIG. 2 is a schematic diagram illustrating a first example of the control and processing executed by the control unit 100. In FIG. 2, the horizontal axis indicates time. In FIG. 2, illustration of the third reception signal S3 and the fourth reception signal S4 input to the second conversion unit 52 is omitted and the first reception signal 51 and the second reception signal S2 input to the first conversion unit 51 are mainly illustrated. However, a description similar to what is described below using FIG. 2 applies to the third reception signal S3 and the fourth reception signal S4.

The upper graph in FIG. 2 illustrates change over time in the light output from the first emission unit 11. This graph illustrates the emission wavelength of the irradiation light from the first emission unit 11 being swept in a certain wavelength range over a plurality of periods and the emission intensity monotonically changing each period by such wavelength sweeping. The center graph in FIG. 2 illustrates change over time in the input of the first reception signal S1 to the first conversion unit 51. The lower graph in FIG. 2 illustrates change over time in the input of the second reception signal S2 to the first conversion unit 51. Although the center and lower graphs in FIG. 2 illustrate the reception intensity increasing linearly each period by omitting, for convenience, change in the reception intensity based on the absorption spectrum, what is actually exhibited is a waveform such as that illustrated in FIG. 6B where a dip based on the absorption spectrum is superimposed.

Here, as above, the emission intensity changes in conjunction with, for example, the sweeping of the injection current of the semiconductor laser. That is, the change in the emission intensity in FIG. 2 may correspond to the change in the injection current. However, not being limited thereto, the change in the emission intensity may correspond to the change in a sweeping voltage input to any wavelength sweeping mechanism controlled by voltage. Likewise, the change in the reception intensity may correspond to change in a current or change in a voltage according to an output form of the signal by each reception unit.

The control unit 100—for example, the timing adjustment controller 60—controls the first switching unit 41 so the first reception signal S1 is repeatedly input to the first conversion unit 51 only during a first time period T1. When a time period elapsed from the output from the first switching unit 41 switching to the first reception signal S1 reaches the first time period T1, the CPU 80 analyzes the optical spectrum based on the first reception signal S1 converted by the first conversion unit 51 during the first time period T1. More specifically, when the timing adjustment controller 60 acquires the first reception signal S1 converted into the digital signal by the first conversion unit 51 only during the first time period T1, the CPU 80 analyzes the absorption spectrum of the analysis-target component C1 based on the acquired first reception signal S1 at the timing indicated by the black upside-down triangle in FIG. 2.

The timing adjustment controller 60 controls the first switching unit 41 to switch from outputting the first reception signal S1 to outputting the second reception signal S2.

The timing adjustment controller 60 controls the first switching unit 41 so the second reception signal S2 is repeatedly input to the first conversion unit 51 only during a second time period T2. When the timing adjustment controller 60 acquires the second reception signal S2 converted into the digital signal by the first conversion unit 51 only during the second time period T2, the CPU 80 analyzes the absorption spectrum of the gas G1 based on the acquired second reception signal S2 at the timing indicated by the white upside-down triangle in FIG. 2.

In the first example illustrated in FIG. 2, the timing adjustment controller 60 controls the first switching unit 41 so the first time period T1 and the second time period T2 are identical.

The timing adjustment controller 60 again controls the first switching unit 41 to switch from outputting the second reception signal S2 to outputting the first reception signal S1. Afterward, the timing adjustment controller 60 and the CPU 80 repeat the above control and processing. In the first example illustrated in FIG. 2, because the first time period T1 and the second time period T2 are identical, an analysis period of analyzing the absorption spectrum of the analysis-target component C1 and an analysis period of analyzing the absorption spectrum of the gas G1 each become 2T1 and are identical to each other.

Here, with each sweeping period, because a general reception signal has a very low signal strength and a low SN ratio, sweeping needs to be repeated several thousand times. So the same SN ratio is obtained for the above measurement signal and reference signal in the optical spectrum, the sweeping counts—that is, the first time period T1 and the second time period T2—are adjusted according to a design of an optical system. In a situation where the SN ratio due to the optical system is different between the measurement signal and the reference signal, even if the first time period T1 and the second time period T2 are identical to each other, the SN ratios of the measurement signal and the reference signal in the optical spectrum are mutually different. Meanwhile, in a situation where the SN ratio due to the optical system is the same between the measurement signal and the reference signal, when the measurement signal and the reference signal are adjusted to the same sweeping count, the SN ratios of the measurement signal and the reference signal in the optical spectrum are mutually identical. At this time, when the first time period T1 and the second time period T2 are made identical to each other as in the first example illustrated in FIG. 2, the analysis period of the absorption spectrum of the analysis-target component C1 that is the main analysis target of the spectrometry device 1 becomes 2T1, preventing an increased speed of analysis.

In a situation where, for example, the timing adjustment controller 60 controls the second switching unit 42 as in the first example illustrated in FIG. 2 and the CPU 80 executes similar processing on the third reception signal S3 and the fourth reception signal S4, an analysis period of the absorption spectrum of the analysis-target component C2 also becomes 2T1. Therefore, an updating period of the overall spectrometry device 1 that analyzes multiple components also becomes 2T1 and an analysis period twice as long as the first time period T1 that is the acquisition time period of the measurement signal becomes necessary.

Even in a situation of respectively processing two reception signals for each analysis-target component, to shorten the analysis period of the analysis-target component, which is crucial for the spectrometry device 1, the control unit 100 performs the control and processing illustrated in FIG. 3.

FIG. 3 is a schematic diagram illustrating a second example of the control and processing executed by the control unit 100. The three graphs in FIG. 3 respectively correspond to the three graphs in FIG. 2. In FIG. 3 as well, illustration of the third reception signal S3 and the fourth reception signal S4 input to the second conversion unit 52 is omitted and the first reception signal S1 and the second reception signal S2 input to the first conversion unit 51 are mainly illustrated. However, a description similar to what is described below using FIG. 3 applies to the third reception signal S3 and the fourth reception signal S4.

Like the first example in FIG. 2, when the timing adjustment controller 60 acquires the first reception signal S1 converted into the digital signal by the first conversion unit 51 only during the first time period T1, the CPU 80 analyzes the absorption spectrum of the analysis-target component C1 based on the acquired first reception signal S1 at the timing indicated by the black upside-down triangle in FIG. 3.

The timing adjustment controller 60 controls the first switching unit 41 to switch from outputting the first reception signal S1 to outputting the second reception signal S2 at the same time as or after analyzing the absorption spectrum of the analysis-target component C1.

The timing adjustment controller 60 controls the first switching unit 41 so the second reception signal S2 is repeatedly input to the first conversion unit 51 only during the second time period T2. Here, the timing adjustment controller 60 controls the first switching unit 41 so the second time period T2 is shorter than the first time period T1. For example, the timing adjustment controller 60 controls the first switching unit 41 so the second time period T2 is ¼T1.

The timing adjustment controller 60 adds a repetition of the second time period T2 each time the output from the first switching unit 41 switches to the second reception signal S2 and determines whether any of the added repetitions of the second period T2 have arrived at a predetermined time period set in advance by, for example, a user. For example, the predetermined time period may be equal to the first time period or different from the first time period. The predetermined time period is, for example, a time period when the sweeping count of the second reception signal S2 by the timing adjustment controller 60 reaches a defined number of times at which a sufficient SN ratio is obtained for analyzing the optical spectrum.

When it is determined that any of the added repetitions of the second time period T2 have not arrived at the predetermined time period set in advance, the timing adjustment controller 60 again controls the first switching unit 41 to switch from outputting the second reception signal S2 to outputting the first reception signal S1. Afterward, the timing adjustment controller 60 and the CPU 80 repeat the above control and processing.

Meanwhile, when the timing adjustment controller 60 determines that any of the added repetitions of the second period T2 have arrived at a predetermined time period set in advance, the CPU 80 analyzes the optical spectrum based on the second reception signal S2 converted by the first conversion unit 51 during the added repetition of the second time period T2. The timing adjustment controller 60 again controls the first switching unit 41 to switch from outputting the second reception signal S2 to outputting the first reception signal S1 at the same time as or after analyzing the absorption spectrum of the gas G1. Afterward, the timing adjustment controller 60 and the CPU 80 repeat the above control and processing.

As above, when the timing adjustment controller 60 controls the first switching unit 41 so the second time period T2 is ¼T1, the analysis period of analyzing the optical spectrum of the analysis-target component C1 is T1+¼T1. Meanwhile, as illustrated by the white upside-down triangle in FIG. 3, the analysis period of analyzing the absorption spectrum of the gas G1 is, for example, 5T1 to obtain a sweeping count equal to the sweeping count included in the first time period T1.

In this manner, by the timing adjustment controller 60 weighting the switching times of the first switching unit 41 according to the measurement signal and the reference signal, the CPU 80 can, in contrast to the first example, analyze the absorption spectrum of the analysis-target component C1 in a state where the analysis period is ¾T1 shortened. Therefore, even in a situation of processing the first reception signal S1 and the second reception signal S2 with regard to the analysis-target component C1, the analysis period of the analysis-target component C1, which is crucial for the spectrometry device 1, is shortened. This improves an analysis efficiency of the analysis-target component C1 by the spectrometry device 1. Although at this time, the analysis period of the gas G1 becomes, for example, 5T1, because the absorption spectrum of the gas G1 is for wavelength confirmation, there is no need for executing analysis updating as frequently as with the analysis-target component C1 and it is not especially problematic for the analysis period to become long.

By the timing adjustment controller 60 controlling the second switching unit 42 as in the second example illustrated in FIG. 3 and the CPU 80 executing similar processing on the third reception signal S3 and the fourth reception signal S4, the analysis period of the absorption spectrum of the analysis-target component C2 also becomes T1+¼T1. Therefore, an updating period of the overall spectrometry device 1 that analyzes the different analysis-target components C1 and C2 also becomes T1+¼T1 and the CPU 80 can analyze in an analysis period equal to the first time period T1 that is the acquisition time period of the measurement signal.

FIG. 4 is a flowchart illustrating one example of the processing performed by the spectrometry device 1. The description below based on FIG. 4 supposes a situation of processing the first reception signal S1 and the second reception signal S2 based on the first switching unit 41 and the first conversion unit 51. However, similar processing is executed in a situation of processing the third reception signal S3 and the fourth reception signal S4 based on the second switching unit 42 and the second conversion unit 52.

At step S101, the timing adjustment controller 60 of the spectrometry device 1 controls the first switching unit 41 to switch to outputting the first reception signal S1 among outputting the first reception signal S1 and outputting the second reception signal S2.

At step S102, the first conversion unit 51 of the spectrometry device 1 converts the first reception signal S1 output from the first switching unit 41 into the digital signal.

At step S103, the CPU 80 of the spectrometry device 1 analyzes the optical spectrum of the analysis-target component C1 based on the first reception signal S1 converted into the digital signal by the first conversion unit 51 during the first time period T1.

At step S104, the timing adjustment controller 60 of the spectrometry device 1 controls the first switching unit 41 to switch to outputting the second reception signal S2 among outputting the first reception signal S1 and outputting the second reception signal S2.

At step S105, the first conversion unit 51 of the spectrometry device 1 converts the second reception signal S2 output from the first switching unit 41 into the digital signal.

At step S106, the timing adjustment controller 60 of the spectrometry device 1 adds a time period to the second time period T2 and determines whether any of the added repetitions of the second period T2 have arrived at a predetermined time period set in advance. When the timing adjustment controller 60 determines that any of the added repetitions of the second period T2 have arrived at a predetermined time period set in advance, the flow proceeds to step S107. When the timing adjustment controller 60 determines that any of the added repetitions of the second time period T2 have not arrived at the predetermined time set in advance, the flow returns to step S101.

At step S107, when the timing adjustment controller 60 determines that any of the added repetitions of the second period T2 have arrived at a predetermined time period set in advance, the CPU 80 of the spectrometry device 1 analyzes the optical spectrum of the gas G1 based on the second reception signal S2 converted into the digital signal by the first conversion unit 51 during the added repetitions of the second period T2.

In one or more embodiments, according to the above spectrometry device 1, product costs can be reduced even in a situation of processing two reception signals—one based on the measurement light and one based on the reference light—for each analysis-target component. In the spectrometry device 1, by the switching units adjusting the output timings of each reception signal by time division, the measurement signal and the reference signal are digitized by one conversion unit. Therefore, a number of ADC-related circuit components is reduced compared to the prior art, which requires two ADCs.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

For example, dispositions, counts, and the like of each component above are not limited to the content of what is illustrated in the above description and the drawings. The dispositions, counts, and the like of each component may be of any configuration as long as the functions thereof can be realized.

For example, functions and the like included in the means, steps, and the like can be rearranged so as to not logically contradict and a plurality of means, steps, or the like can be combined into one or divided.

For example, one or more embodiments can also be realized as a program written with processing content of realizing the functions of the above spectrometry device 1 or a storage medium recorded with this program. It should be understood that the scope of the present disclosure also includes such.

Figure 5:
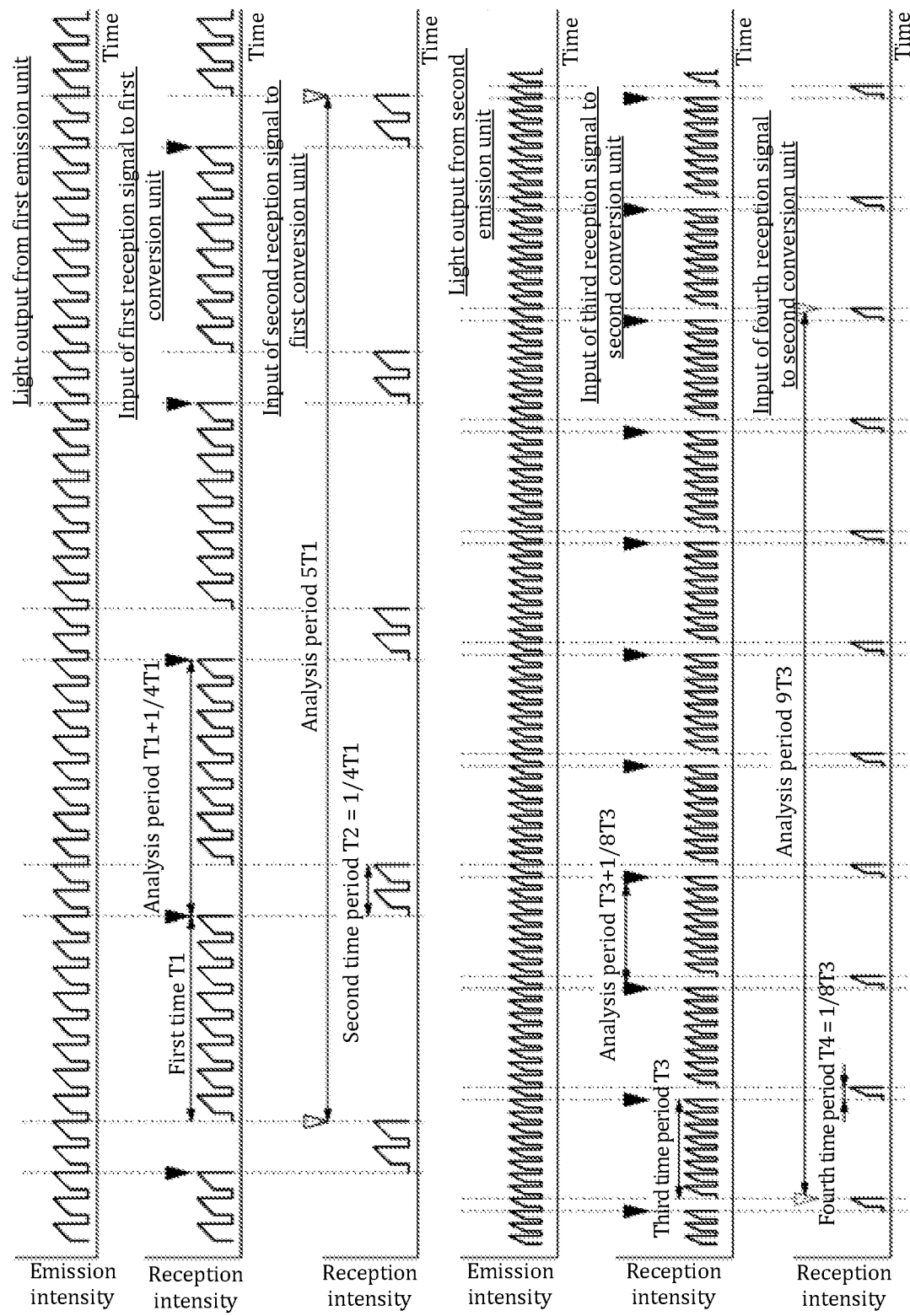
FIG. 5 is a schematic diagram illustrating a third example of the control and processing executed by the control unit.

For example, the example of the control and processing executed by the control unit 100 is not limited to the first example and the second example respectively described while referring to FIGS. 2 and 3. FIG. 5 is a schematic diagram illustrating a third example of the control and processing executed by the control unit 100. As illustrated in FIG. 5, the wavelength sweeping time periods of the first light emitting unit 11 and the second light emitting unit 12 may be different from each other with regard to the two types of analysis-target components C1 and C2 of different analytical wavelengths. Moreover, a ratio of the second time period T2 relative to the first time period T1 and a ratio of the fourth time period T4 that is the acquisition time period of the fourth reception signal S4 relative to the third time period T3 that is the acquisition time period of the third reception signal S3 may be different from each other.

In the third example illustrated in FIG. 5, when the timing adjustment controller 60 controls the second switching unit 42 so the fourth time period T4 is ⅛T3, the analysis period of analyzing the absorption spectrum of the analysis-target component C2 is T3+⅛T3 as illustrated by the black upside-down triangle in FIG. 5. Meanwhile, as illustrated by the white upside-down triangle in FIG. 5, the analysis period of analyzing the absorption spectrum of the gas G2 is, for example, 9T3 to obtain a sweeping count equal to the sweeping count included in the third time period T3.

As above, by changing the wavelength sweeping time periods for each emission unit and shortening the acquisition time periods of each reference signal to shorten the analysis periods of the analysis-target components, the spectrometry device 1 can operate asynchronously in terms of the two types of analysis-target components C1 and C2 of different analytical wavelengths. This enables the spectrometry device 1 to optimize the analysis period for each analysis-target component based on the analysis-target component, the semiconductor laser element that is used, and the like.

As described above, in one or more embodiments, the description is limited to TDLAS. However, the spectrometry device 1 can be applied to any analyzer that performs spectrometry of any analysis target based on repeated sweeping signals.

As described above, in one or more embodiments, the optical spectrum is described as including the absorption spectrum. However, the present invention is not limited thereto. The spectrometry device 1 may analyze the analysis-target components using any spectrometry method other than such an absorption spectrometry method. The spectrometry method may include, for example, fluorescence spectrometry or Raman spectrometry. For example, in fluorescence spectrometry, the optical spectrum includes a fluorescent spectrum. For example, in Raman spectrometry, the optical spectrum includes a Raman spectrum.

As described above, in one or more embodiments, the first reception signal S1 and the third reception signal S3 are described as respectively including the optical-spectrum information relating to the analysis-target components C1 and C2 and the second reception signal S2 and the fourth reception signal S4 are described as respectively including the optical-spectrum information relating to the reference gases G1 and G2. However, the present invention is not limited thereto. Each reception signal may include optical-spectrum information relating to any target. For example, new analysis-target components may be respectively enclosed instead of the reference gases G1 and G2 and the second reception signal S2 and the fourth reception signal S4 may also include optical-spectrum information relating to the analysis-target components like the first reception signal S1 and the third reception signal S3. In this situation, for example, an analysis target with a higher priority is analyzed based on the first reception signal S1 or the third reception signal S3 and an analysis target with a lower priority is analyzed based on the second reception signal S2 or the fourth reception signal S4.

1 Spectrometry device
10 Laser controller
11 First emission unit
12 Second emission unit
21 First reference cell
22 Second reference cell
31 First reception unit
32 Second reception unit
33 Third reception unit
34 Fourth reception unit
41 First switching unit
42 Second switching unit
51 First conversion unit
52 Second conversion unit
60 Timing adjustment controller
71 First storage unit
72 Second storage unit
73 Third storage unit
74 Fourth storage unit
80 CPU
100 Control unit
C1, C2 Analysis-target component
G Gas to be measured
G1, G2 Gas
S1 First reception signal
S2 Second reception signal
S3 Third reception signal
S4 Fourth reception signal
T1 First time period
T2 Second time period
T3 Third time period
T4 Fourth time period

What is claimed is:
1. A spectrometry device, comprising:
a processor that:
acquires a first reception signal and a second reception signal that respectively include information relating to an optical spectrum, controls switching between outputting the first reception signal and outputting the second reception signal, converts the switched-to first reception signal or the second reception signal into a digital signal, causes a second time period to be shorter than a first time period when converting the switched-to first reception signal or the second reception signal into the digital signal, wherein
- conversion of the first reception signal is repeated during the first time period, and
- conversion of the second reception signal is repeated during the second time period, adds a repetition of the second time period, determines whether the added repetition of the second time period arrives at a predetermined time period set in advance, and analyzes the optical spectrum based on the converted second reception signal during the added repetition of the second time period when it is determined that the added repetition of the second time period arrived at the predetermined time.

2. The spectrometry device of claim 1, wherein the processor further:
analyzes the optical spectrum based on the converted first reception signal when the first time period is reached from switching to the first reception signal from the second reception signal.

3. The spectrometry device of claim 2,
wherein the first reception signal includes information that relates to an absorption spectrum of an analysis-target component in a gas to be measured, and
wherein the second reception signal includes information on an absorption spectrum of a gas that is identical to the analysis-target component in the gas to be measured and has a known concentration.

4. The spectrometry device of claim 1, wherein the predetermined time period is equal to the first time period.

5. The spectrometry device of claim 4,
wherein the first reception signal includes information that relates to an absorption spectrum of an analysis-target component in a gas to be measured, and
wherein the second reception signal includes information on an absorption spectrum of a gas that is identical to the analysis-target component in the gas to be measured and has a known concentration.

6. The spectrometry device of claim 1,
wherein the first reception signal includes information that relates to an absorption spectrum of an analysis-target component in a gas to be measured, and
wherein the second reception signal includes information on an absorption spectrum of a gas that is identical to the analysis-target component in the gas to be measured and has a known concentration.

7. A spectrometry method by a spectrometry device, comprising:
acquiring a first reception signal and a second reception signal that respectively include information relating to an optical spectrum;

switching between outputting the first reception signal and outputting the second reception signal;

converting the switched-to first reception signal or second reception signal into a digital signal;

causing a second time period to be shorter than a first time period when converting the switched-to first reception signal or the second reception signal into the digital signal, wherein conversion of the first reception signal is repeated during the first time period, and conversion of the second reception signal is repeated during the second time period;

adding a repetition of the second time period;

determining whether the added repetition of the second time period arrives at a predetermined time period set in advance; and analyzing the optical spectrum based on the converted second reception signal during the added repetition of the second time period when it is determined that the added repetition of the second time period arrived at the predetermined time.

8. The spectrometry method of claim 7, further comprising:
analyzing the optical spectrum based on the converted first reception signal when the first time period is reached from switching to the first reception signal from the second reception signal.

9. The spectrometry method of claim 8,
wherein the first reception signal includes information that relates to an absorption spectrum of an analysis-target component in a gas to be measured, and
wherein the second reception signal includes information on an absorption spectrum of a gas that is identical to the analysis-target component in the gas to be measured and has a known concentration.

10. The spectrometry method of claim 7, wherein the predetermined time period is equal to the first time period.

11. The spectrometry method of claim 7,
wherein the first reception signal includes information that relates to an absorption spectrum of an analysis-target component in a gas to be measured, and
wherein the second reception signal includes information on an absorption spectrum of a gas that is identical to the analysis-target component in the gas to be measured and has a known concentration.

* * * * *